United States Patent [19]
Seiler

[11] Patent Number: 5,878,443
[45] Date of Patent: Mar. 9, 1999

[54] CONVERTIBLE PROTECTIVE COVER FOR A MASK

[76] Inventor: Douglas A. Seiler, 127 Iolanthus Ave., Novato, Calif. 94945

[21] Appl. No.: 857,142

[22] Filed: May 15, 1997

[51] Int. Cl.⁶ .............................. A61F 9/02; A45C 11/04
[52] U.S. Cl. ........................................ 2/426; 2/452; 206/5
[58] Field of Search ............................ 206/5; 2/426, 434, 2/438, 452, 454; 224/255

[56] References Cited

U.S. PATENT DOCUMENTS

| | | |
|---|---|---|
| 4,232,808 | 11/1980 | Gray . |
| 4,339,062 | 7/1982 | Witt, Jr. . |
| 4,649,973 | 3/1987 | Uchin . |
| 4,910,806 | 3/1990 | Baker et al. . |
| 4,919,257 | 4/1990 | Perretta ..................................... 206/5 |
| 4,953,695 | 9/1990 | Tallman . |
| 5,014,846 | 5/1991 | Walker et al. . |
| 5,102,216 | 4/1992 | Mitchell . |
| 5,151,778 | 9/1992 | Conley . |
| 5,213,241 | 5/1993 | Dewar et al. ............................ 206/5 X |
| 5,299,682 | 4/1994 | Tater ........................................ 206/5 |
| 5,344,002 | 9/1994 | Baczkowski . |
| 5,366,072 | 11/1994 | Goldenberg . |
| 5,593,024 | 1/1997 | Seiler . |
| 5,687,837 | 11/1997 | Seiler ........................................ 206/5 |

*Primary Examiner*—Michael A. Neas
*Assistant Examiner*—Shirra L. Jenkins
*Attorney, Agent, or Firm*—Foley & Lardner

[57] ABSTRACT

A case for a mask includes a first panel secured to a second panel to form a pouch into which the mask may be inserted and removed. The second panel may include a pair of overlapping panel sections defining an opening for insertion of the mask. Apertures on either side of the case accommodate passage of a strap attached to the mask. Alternatively, straps may be permanently secured to the case. Closure elements on either side of the opening maintain the case in a closed position. The case may be positioned behind the user's head when the mask is being used, cushioning the strap, and may be inverted into a storage configuration to cover at least the mask lens. The closure elements are oriented in mutually facing relation in both configurations to maintain the case closed. Panels of the case may be made of floatable synthetic materials or may include light-weight or net materials to promote drying of the case and mask following use.

11 Claims, 8 Drawing Sheets

FIG. 34

CONVERTIBLE PROTECTIVE COVER FOR A MASK

FIELD OF THE INVENTION

The present invention relates generally to the field of protective cases or covers for masks, such as diving or ski masks. More particularly, the invention relates to a soft, flexible case for a mask that can be worn behind the user's head when the mask is in use and which may be inverted for storing the mask without detaching the mask from the case.

BACKGROUND OF THE INVENTION

Masks commonly used by underwater divers, snorkeling swimmers, downhill skiers and the like, typically include a front mask portion with a single or double viewing window or lens, and a strap designed to encircle the user's head to hold the mask tightly in place over the user's eyes. The mask portion is usually made of a flexible rubber composition that seals against the user's skin when in use to prevent water, snow or other materials from entering into the mask and obscuring the user's vision. Such masks may also fit over the user's nose as well. Attachment rings or similar structures on either side of the mask permit the strap to be firmly attached and adjusted to provide the desired level of sealing and comfort for the user. Increasingly, such masks include fairly sensitive viewing windows or lenses, sometimes including corrective optics, that can be easily scratched or otherwise damaged when the mask is not in use.

Despite the risk of damage to the mask viewing window, however, many divers, snorkelers and skiers care for such masks simply by rinsing or wiping them after use and storing them along with other equipment, such as in an equipment bag or the like. In such cases, the lenses of the masks may be inadvertently scratched, broken or otherwise damaged between uses. While special bags may be used for storing the mask individually, such bags are separable from the mask and must be located for storage of the mask following use. The mask remains, therefore, exposed to damage upon return to a dive boat, shore or lodge until the bag can be located and the mask inserted therein.

Another drawback with conventional sport masks is that the strap used to secure the mask to the user's head, typically an elastic rubber or similar flexible strip, may bind on the user's hair or otherwise cause discomfort to the user along the region where it contacts the back of the user's head. Various solutions have been proposed to isolate such straps from the user's hair and to provide a limited degree of padding between the strap and the user's head. In one known arrangement, an elastic panel is secured to a pair of ribbon members that are designed for attachment to the mask. In another known device, a removable elastic panel is designed to receive a portion of a mask strap and to remain attached to the strap both during use and storage. Such elastic panels provide a region over which pressure exerted by the strap may be distributed, reducing discomfort to the user. However, such panels do not provide for storage of the mask, and must generally be placed, along with the mask and strap, in an equipment bag or the like following use, again exposing the mask lenses to potential damage.

There is a need, therefore, for an improved case for sports masks capable of offering convenient storage of a mask when not in use, and which need not be detached from the mask when secured to the user's head. Moreover, there is a need for a mask case that provides padding or otherwise improves the comfort level for the user when wearing the mask, by distributing loads exerted by the securing strap behind the user's head then the mask is worn.

SUMMARY OF THE INVENTION

The present invention features a novel case designed to respond to these needs. The case provides a convenient storage bag or envelope for the mask when not in use and may remain attached to the mask strap, positioned comfortably behind the user's head when the mask is worn. The case may be formed with apertures for passing the strap therethrough, or may be permanently secured to the straps to form an attachment assembly fitted to the mask. In a preferred configuration, the case collapses to a relatively small, padded panel that provides padding for the mask strap, and is inverted over the mask as the mask is inserted therein following use. The case may be made of a variety of materials, including rubber or other synthetic compositions that provide added buoyancy to the mask, thereby preventing or inhibiting sinking of the mask if dropped into water.

Thus, in accordance with a first aspect of the invention, a case is provided for a mask of the type including a frame, a lens supported in the frame, and a strap attached to the frame and configured to partially encircle the head of a user to hold the frame against the user's face. The case includes flexible front and rear panels and first and second side apertures. The front panel is configured to bear against the user's head when worn. The rear panel is secured to the front panel along a border region to define a pouch having a central opening through which the mask may be inserted into and removed from the pouch. The side apertures are defined on either side of the central opening for receiving the strap for holding the case on a central region of the strap. The case is attachable to the strap and positionable in a first, in-use configuration wherein the case is substantially flattened for wearing behind the user's head, and in a second, storage configuration wherein the case envelops at least the mask lens. The case may include a gusset structure interposed between the front and rear panels to increase the volume of the case in the storage configuration.

In accordance with another aspect of the invention, a case is adapted for a mask including a frame configured to fit sealingly around a portion of a user's face, at least one lens supported in the frame, and first and second strap attachment structures for receiving and cooperating with an attachment strap to maintain the mask securely on the user's head, one attachment structure being disposed on either side of the frame. The case includes flexible front and rear panels, and first and second straps. The front panel is configured to bear against the back of the user's head when worn, while the rear panel is secured to the front panel and defines with the front panel an invertible pouch. The rear panel further defines an opening through which the mask may be inserted into and removed from the pouch. The first and second straps are configured for attachment to the first and second strap attachment structures respectively. The first strap is secured to a first side region of the pouch and extends from the pouch toward the mask when secured to the first strap attachment structure. The second strap is secured to a second side region of the pouch opposite from the first side region and extends from the pouch toward the mask when secured to the second strap attachment structure. In a particularly preferred embodiment, the first and second straps are elastic members. Also, the first and second straps preferably include a hook and loop fastening system defined by regions which overlie one another when the mask and case are worn by the user.

The invention also provides a convertible mask case including a flexible first panel, a flexible second panel secured to the first panel and a strap system. The second panel defines with the first panel a convertible pouch. The pouch includes an opening through which the mask may be inserted into and removed from the pouch. The strap system includes first and second strap portions configured for attachment to the pouch and to the first and second strap attachment structures respectively. The first and second strap portions extend between the pouch and the first and second attachment structures when the mask and pouch are worn around the user's head. The pouch is collapsible into a first, worn configuration wherein the pouch fits securely against the user's head and a second, storage configuration wherein the pouch envelopes over the mask to cover at least the lens.

BRIEF DESCRIPTION OF THE DRAWINGS

The present invention will become more fully understood from the following detailed description, taken in conjunction with the accompanying drawings, wherein like reference numerals refer to like parts, in which.

DETAILED DESCRIPTION OF PREFERRED EMBODIMENTS

Figure 1:
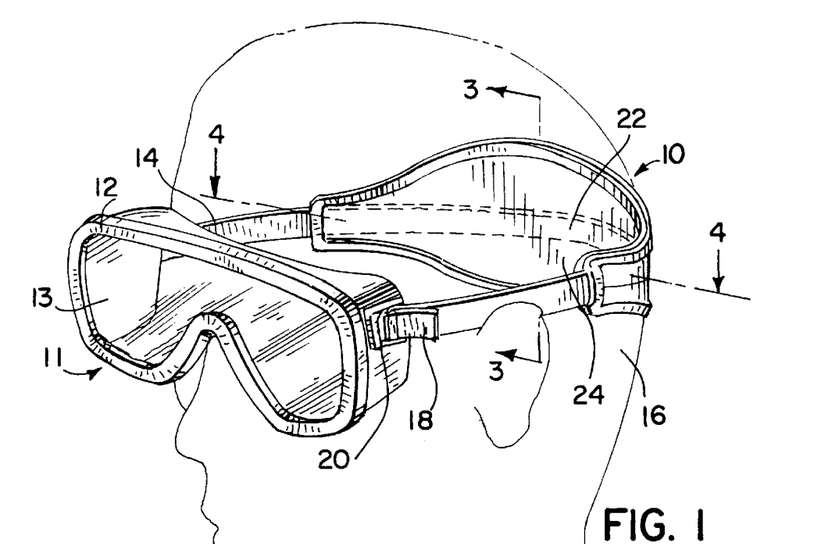
FIG. 1 is a perspective view of a flexible case in accordance with a first preferred embodiment, the case being slidingly received over a portion of a strap of a mask supported on a user's head.
Figure 2:
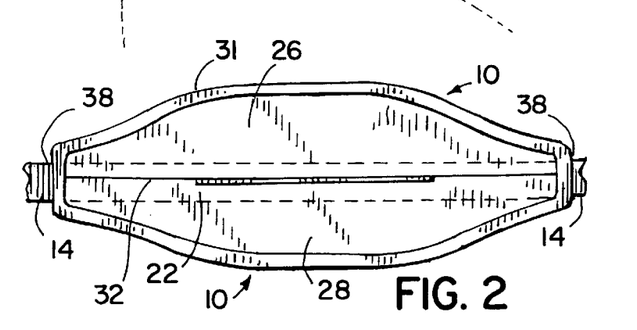
FIG. 2 is a front elevational view of the case of FIG. 1 shown in its folded position and illustrating panels defining an opening for inserting the mask therein, in their joined or closed position.

Turning now to the figures and referring first to FIG. 1, a soft-flexible case for a mask is illustrated and designated generally by the referenced numeral 10. Case 10 is shown coupled to a mask 11 via a flexible strap 14. Strap 14 extends around the head 16 of a user, positioning case 10 in a folded position tightly behind the users head 16. Mask 11 may be of any conventional type, including a shell or frame 12 made of a soft flexible material supporting a lens 13. In use as illustrated in FIG. 1, strap 14 holds shell 12 of mask 11 firmly against the users face to seal the mask and prevent the intrusion of water behind lens 13. Ends 18 of strap 14 are secured to attachment ring assemblies 20 on either side of the mask. Ring assemblies 20 may be of any known type, and generally provide for adjustability of tension of strap 14 by doubling the end of the strap back upon itself such that the end of strap 14 exits toward the rear of attachment ring assembly 20. In the folded, cushioning position illustrated in FIG. 1, case 10 is secured along a central region 22 of strap 14 located behind the users head 16.

Referring now more specifically to the preferred construction of the first embodiment illustrated in FIGS. 1 through 7, case 10 includes a front panel 24 attached to upper and lower rear panels 26 and 28, respectively. A front border strip 30 extends around a peripheral of front panel 24, while a similar rear border strip 31 extends around both upper and rear panels 26 and 28. Upper and lower rear panels 26 and 28 meet in a central region and overlap one another, defining an opening 32 in the rear of case 10 through which mask 11 may be inserted and removed as described more fully below. A first closure element, preferably in the form of a hook and loop closure panel 33 is provided along an inner lower edge 34 of upper rear panel 26. A cooperating closure element 35, also preferably a hook and loop closure panel is provided along an outer upper edge 36 of lower rear panel 28 in facing relation to element 33, providing a positive closure means for case 10 both in the folded configuration illustrated in FIGS. 1–4 as well as in an inverted, storage position described below in reference to FIGS. 6 and 7. In addition to opening 32, the embodiment of case 10 illustrated in FIGS. 1 through 12 includes left and right side apertures 38 through which strap 14 is slidingly inserted upon assembly of case 10, strap 14 and mask 11. Front and rear panels 24, 26 and 28 thus define an invertible pouch for storage of mask 11 as described below.

Figure 3:
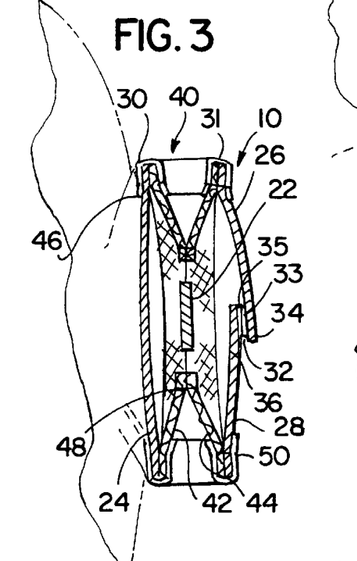
FIG. 3 is a sectional view along line 3—3 of FIG. 1 illustrating a preferred construction of the case.
Figure 4:
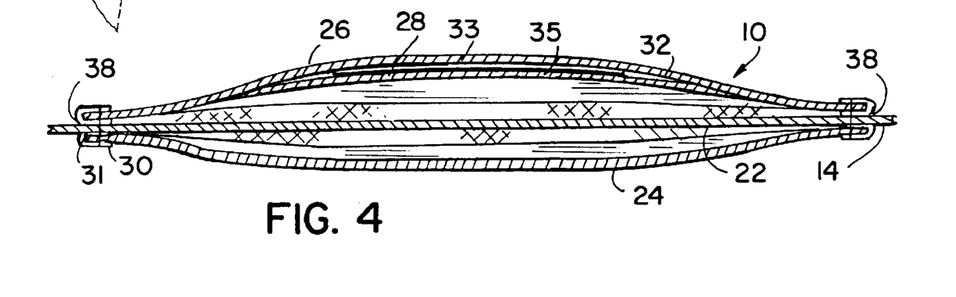
FIG. 4 is a sectional view along line 4—4 of FIG. 1, illustrating the internal construction of the case.

FIGS. 3 and 4 illustrate a preferred construction of the elements described above, in addition to a central gusset 40 preferably provided in case 10 to readily expand its internal capacity. As shown in FIG. 3, front panel 24 is joined, such as by stitching, to a front gusset panel 42 which has a generally elongated annular shape, while rear panels 26 and 28 are joined to a similar rear gusset panel 44. A front border hem 46 is thus formed along upper and lower regions along which front panel 24 and front gusset panel 42 are joined, with front border 30 being captured around the joint of these two panels by the same stitching. Front gusset 42 is joined to a rear gusset panel 44 along a gusset hem 48. Rear gusset panel 44 is, in turn, joined to upper and lower rear panels 26 and 28, such as by a border hem 50, which preferably also captures rear border 31 and holds border 31 in place around the joint. As will be appreciated by those skilled in the art, gusset hem 48 is discontinuous in the region of side apertures 38 in order to provide a gap between gusset panels 42 and 44, thereby defining apertures 38. As shown in FIGS. 3 and 4, when assembled with strap 14, case 10 extends along strap 14 and is stretched and flattened somewhat by tension of strap 14 when pulled taut behind the user's head. However, strap 14 remains somewhat free to stretch through side apertures 38.

Front panel 24, rear panels 26 and 28, gusset panels 42 and 44, and borders 30 and 31 are all preferably made of flexible sheet materials, such as fabrics, synthetic composite materials and the like. In a particularly preferred embodiment, front panel 24 is made of an open or close-cell neoprene, as are rear panels 26 and 28. Gusset panels 42 and 44 may be made of a lighter-weight synthetic fabric, or may comprise open netting. As will be appreciated by those skilled in the art, the use of synthetic foam materials, such as neoprene for front and rear panels 24, 26 and 28 provides added buoyancy to case 10, preferably sufficient to maintain mask 11 afloat, or at least to significantly reduce the tendency of mask 11 to sink in water (e.g., when case 10 is used with a diving mask and the mask is inadvertently dropped by a diver). In addition, the use of light-weight synthetic fabrics for gusset panels 42 and 44 allows case 10 and mask 11 to dry quickly once removed from the water and stored in their storage position as described below. Moreover, it should be noted that the use of foam-type materials for front panel 24 provides a cushion for added comfort against the user's head when in use, while the use of relatively light-weight materials for gusset panels 42 and 44 reduces the overall thickness of case 10 when in its folded, in-use position as shown in FIGS. 1 through 4.

Figures 5, 6, 7, 8:
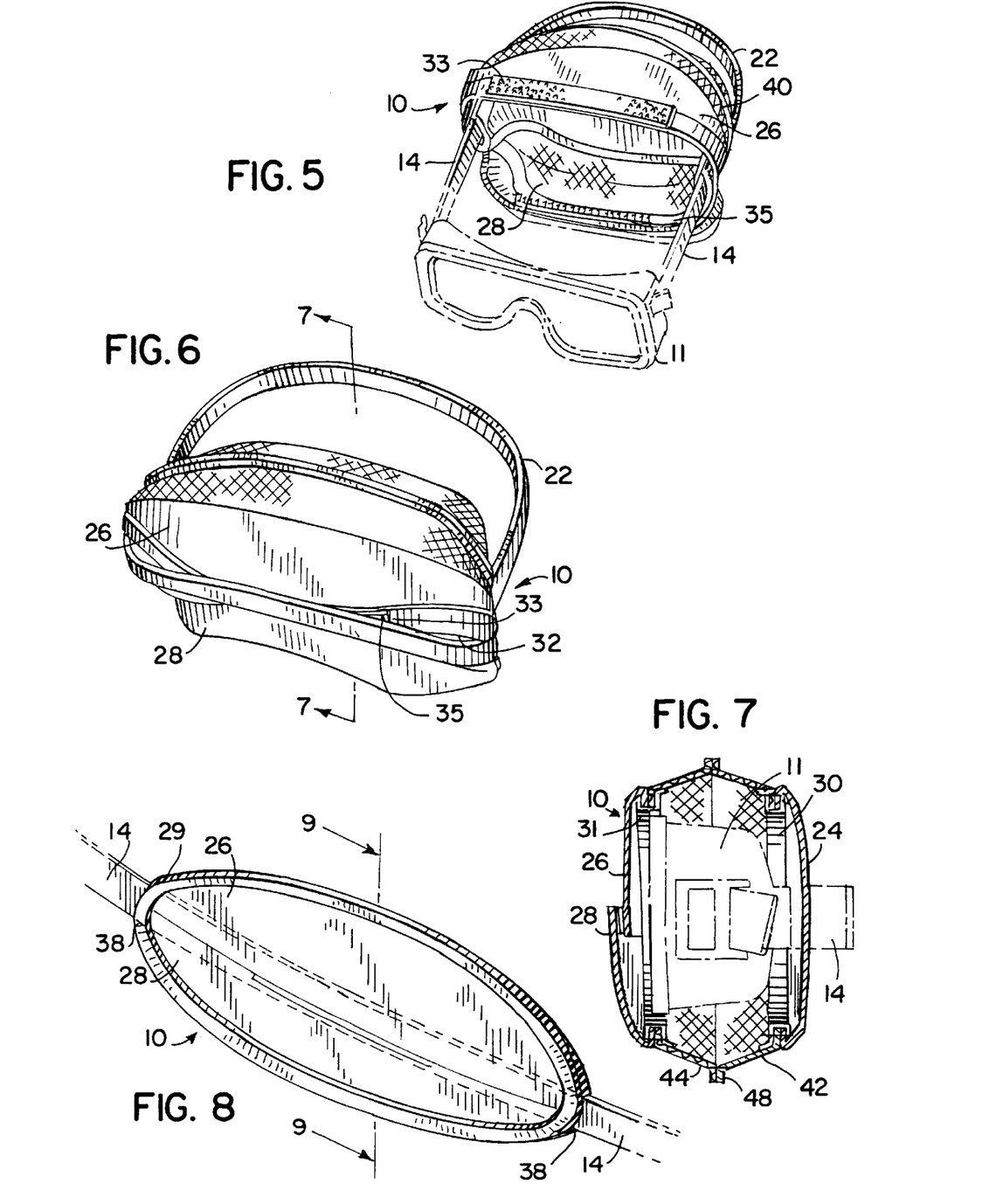
FIG. 5 is a perspective view of the case of FIG. 1 in a first phase of inversion for insertion of the mask therein.
FIG. 6 is a perspective view of the case following insertion of the mask therein.
FIG. 7 is a sectional view of the case along line 7—7 of FIG. 6, showing the configuration of the case when the mask is lodged or stored therein, and illustrating the manner in which the opening of the case is closed over the mask.
FIG. 8 is a perspective view of a variant of the first preferred embodiment, wherein the construction of the case.

Following use of mask 11, a user inserts mask 11 into case 10 as follows. As best illustrated in FIG. 5, the user first separates closure elements 33 and 35, such as by pulling upper and lower rear panels 26 and 28 apart. Borders 30 and 31 are then pressed inwardly and upper and lower rear panels 26 and 28 are folded back over the borders, effectively inverting case 10 on itself and expanding central gusset 40. Mask 11 is then moved rearwardly into the pouch defined by the now inwardly facing exterior panels of case 10. Central region 22 of strap 14 may be pulled rearwardly, sliding strap 14 through side apertures 38 to further draw mask 11 into case 10. Once mask 11 is fully enveloped by case 10, upper and lower rear panels 26 and 28 may be pulled toward one another as shown in FIG. 6. It should be noted that due to the inversion of case 10 as it is converted from its folded, in-use position to its storage position, closure elements 33 and 35 once again are located in a mutually facing and cooperating position and may be rejoined as shown in FIG. 6. As best illustrated in FIG. 7, once inverted and closed around mask 11, exterior features of case 10 will be located in an interior region of the case. Thus, front and rear borders 30 and 31 bound mask 11 and upper and lower rear panels 26 and 28 are rejoined over mask 11, thereby protecting the mask lens from damage through inadvertent contact with other equipment. It should also be noted that in the embodiment illustrated in FIGS. 1 through 7, central region 22 of strap 14 is located outside case 10 when placed in its storage position, thus, the user may grasp strap 14 for transport of case 10 with mask 11 or may use strap 14 for hanging the case from convenient hooks or the like.

Figure 9:
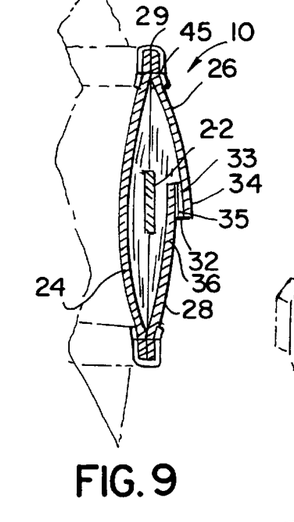
FIG. 9 is a sectional view of the case of FIG. 8 along line 8—8, illustrating the several components of this embodiment.
Figure 10:
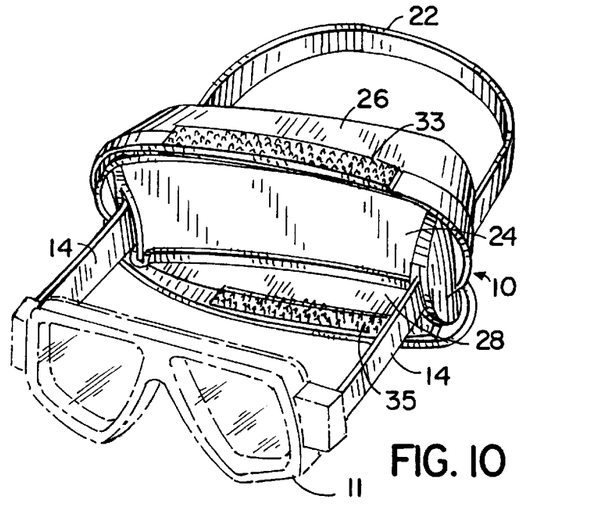
FIG. 10 is a perspective view of the case of FIG. 8 in a first phase of inversion for insertion of the mask therein.
Figures 11, 12, 13:
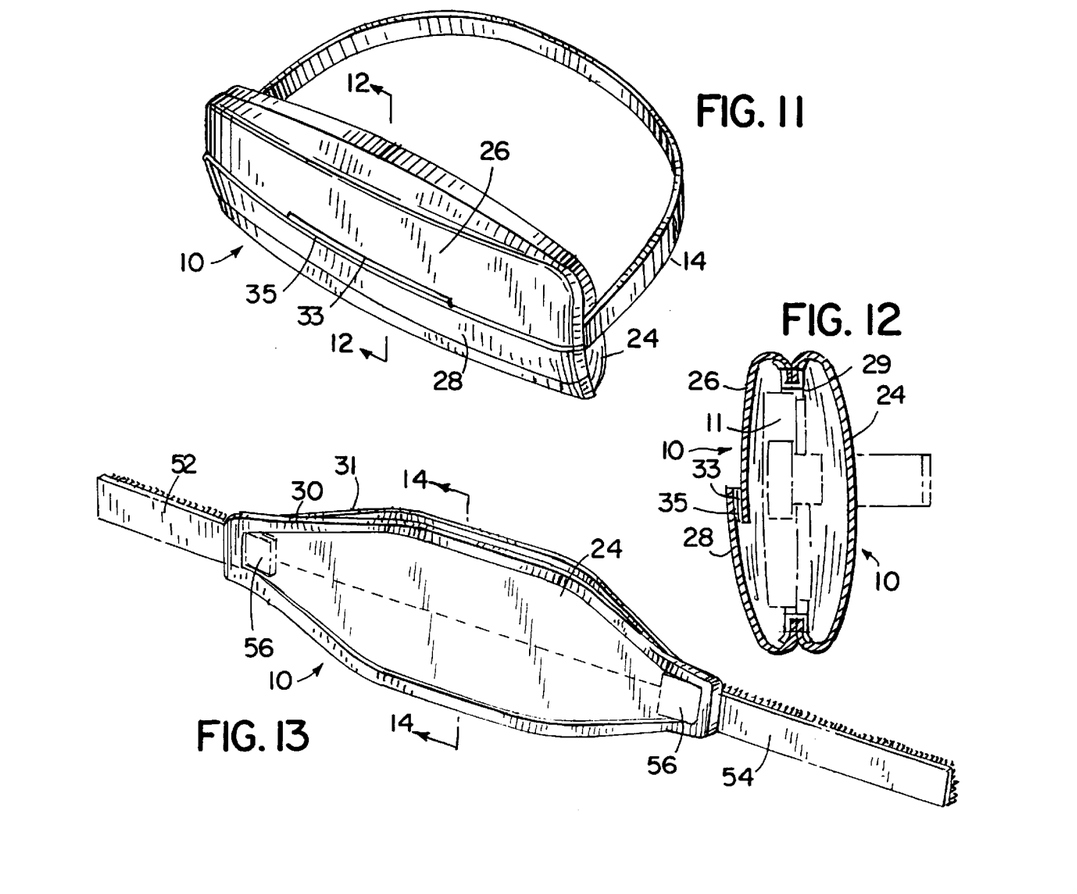
FIG. 11 is a perspective view of the case of FIG. 8 following full insertion of the mask therein.
FIG. 12 is a sectional view of the case of FIG. 11 along line 12—12, showing the mask fully inserted into the case.
FIG. 13 is a front perspective view of a second preferred embodiment of the invention, wherein a pair of straps are permanently secured to either side of the case.

FIGS. 8 through 12 illustrate a variant of the case described above wherein central gusset 40 is essentially eliminated. Thus, as shown in FIGS. 8 and 9, case 10 includes a front panel 24 and upper and lower rear panels 26 and 28 bounded by a single border strip 29. While border strip 29 preferably completely surrounds both front panel 24 and rear panels 26 and 28, border 29 and the front and rear panels are separated along end regions corresponding to side apertures 38, permitting passage of strap 14 therethrough as described above. A single border hem 45 is preferably provided for joining front panel 24 to rear panels 26 and 28 and for capturing border 29 around the region where these panels are joined. Closure elements 33 and 35 are provided along lower edge 34 and upper edge 36 of upper and lower rear panels 26 and 28, respectively. As in the previous embodiment, these closure elements are preferably hook and loop fastener strips secured to the rear panels, such as by gluing, stitching or any other suitable means. Case 10 is assembled with strap 14 as before, by passing strap 14 through apertures 38 and lodging a central region 22 of strap 14 within case 10 in its folded, in-use configuration shown in FIGS. 8 and 9. Following use, when a user desires to store mask 11 within case 10, closure elements 33 and 35 are separated from one another, and upper and lower rear panels 26 and 28 are folded up over border 29 in order to invert case 10, as illustrated in FIG. 10. Strap 14 may then be pulled rearwardly to draw mask 11 into case 10. The case may then be closed over the mask and closure elements 33 and 35 may again be joined as shown in FIG. 11. As in the previous embodiment, external features of case 10 are located within the interior of the case when placed in its storage position, as shown in the sectional view of FIG. 12. Thus, border 29 generally bounds mask 11 and closure elements 33 and 35 secure upper and lower rear panels 26 and 28 to one another to maintain these panels in a protective position over mask 11.

In an alternative configuration of case 10, illustrated in FIGS. 13 through 23, fastening strips may be secured directly to case 10 in order to define a padded case and attachment system, obviating the need for a separate strap as in the previous embodiments. Thus, in an alternative preferred embodiment illustrated in FIG. 13, case 10 includes first and second attachment straps 52 and 54, respectively, permanently secured to case 10, such as by stitching along attachment regions 56. The general construction of case 10 in this embodiment may be substantially identical to that described above with reference to FIGS. 1 through 7, except that front panel 24 and upper and lower rear panels 26 and 28 may be completely joined along side regions, thereby eliminating side apertures 38 from the previous embodiment. Instead, at similar locations of case 10, attachment regions 56 define points of anchoring for attachment straps 52 and 54. Other features, such as front panel 24, rear panels 26 and 28 and gusset panels 42 and 44, along with borders surrounding these panels and their corresponding hems, may be substantially identical to those described with regard to the previous embodiment, as illustrated in the sectional view of FIG. 14.

Figures 14, 15, 16:
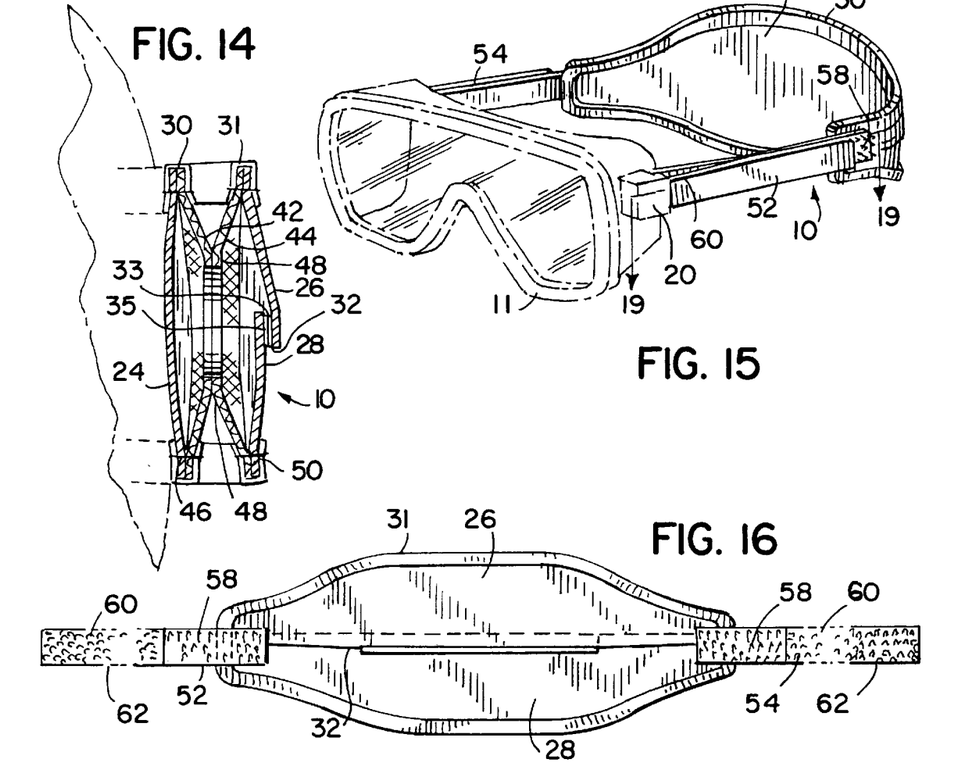
FIG. 14 is a sectional view of the case of FIG. 13 along line 14—14, illustrating a preferred construction of this embodiment.
FIG. 15 is a perspective view of the embodiment of FIG. 13 shown attached to a mask.
FIG. 16 is a back elevation view of the case of FIG. 13 illustrating a preferred arrangement of the attachment straps and showing the panels of the case defining its opening in their joined position.
Figure 19:
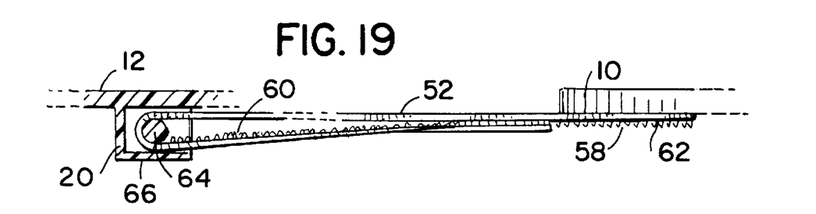
FIG. 19 is a sectional view of the case of FIG. 13 along line 19—19 of FIG. 15, illustrating a preferred method for attaching the mask to an attachment point of a mask.

FIGS. 15 and 16 illustrate a preferred arrangement for securing attachment straps 52 and 54 to mask 11. As best shown in FIG. 16, each attachment strap preferably includes a first region 58 defining a first type of attachment mechanism, such as a hook-type attachment region, and a second region 60 distal from case 10 with respect to regions 58, defining a second, cooperating attachment structure, such as a loop-type attachment strip. Regions 58 and 60 are designed to be located along an outer side 62 of straps 52 and 54 and are located in mutually facing relation when attached to mask 11 as shown in FIG. 15. As illustrated in that figure, straps 52 and 54 are attached to mask 11 by routing the strip first through an attachment assembly 20 provided on either side of mask 11, and folding straps 52 and 54 back toward case 10 so that region 60 of each strip at least partially overlies region 58, permitting attachment of these regions to one another. FIG. 19 provides a sectional view along line 19—19 of FIG. 15 illustrating this attachment system. As shown in FIG. 19, attachment assembly 20 may conveniently include a post 64 at least partially surrounded by a shroud 66. Straps 52 and 54, secured to case 10, are passed around post 64 and folded back toward case 10 to bring regions 58 and 60 into alignment. In a particularly preferred embodiment, straps 52 and 54 are made of an elastic material or an elasticized fabric to which regions 58 and 60 are either applied, such as by gluing or stitching, or on which regions 58 and 60 are directly formed. Such elastic materials provide a comfortable yet snug fit for mask 11 on the user's head, while holding case 10 securely in place during use of mask 11.

Figures 17, 18:
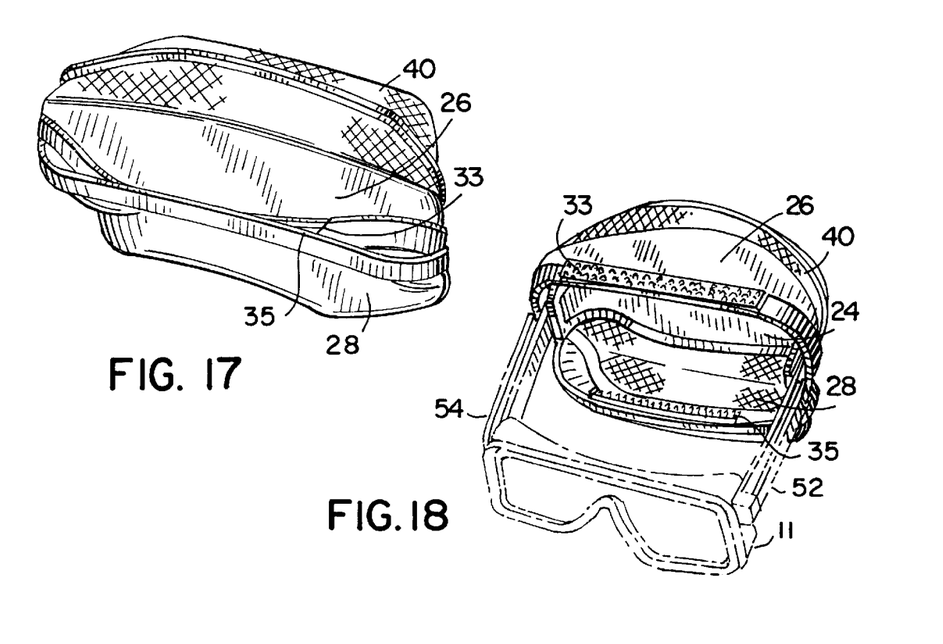
FIG. 17 is a perspective view of the case of FIG. 13 closed over a mask.
FIG. 18 is a perspective view of the case of FIG. 17 removed from the mask and partially folded into its storage position.

In this embodiment of case 10, insertion of mask 11 into the case for storage results in enclosing both mask 11 and straps 52 and 54 within case 10. Thus, as shown in FIG. 17, insertion of mask 11 into case 10 begins, as before, by separation of closure elements 33 and 35 from one another and by inversion of case 10 to expand central gusset 40 outwardly. Mask 11 may then be inserted into inverted case 10, along with attachment strips 52 and 54. Once fully inserted into case 10, mask 11 may be enveloped by the case and closure elements 33 and 35, once again in mutually facing relation, may be joined to completely enclose mask 11 within the case, as illustrated in FIG. 18.

Figure 20:
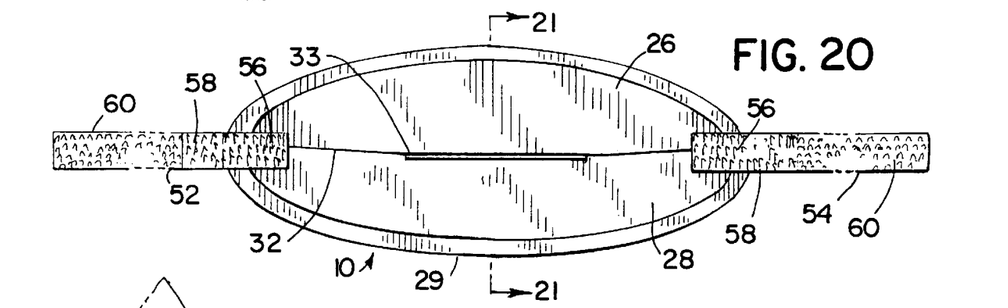
FIG. 20 is a back elevation view of a variant of the second embodiment of FIG. 13.
Figure 21:
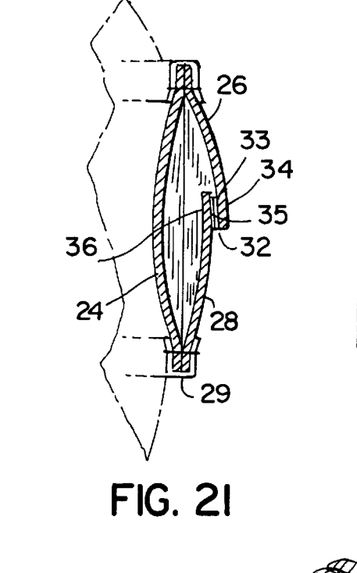
FIG. 21 is a sectional view along line 21—21 of FIG. 20 illustrating the various components of this configuration of the case.
Figure 22:
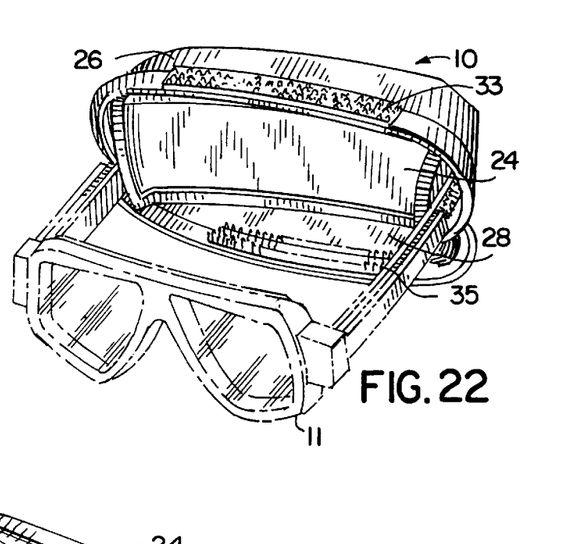
FIG. 22 is a perspective view of the case of FIG. 20, partially inverted for insertion of the mask therein.
Figure 23:
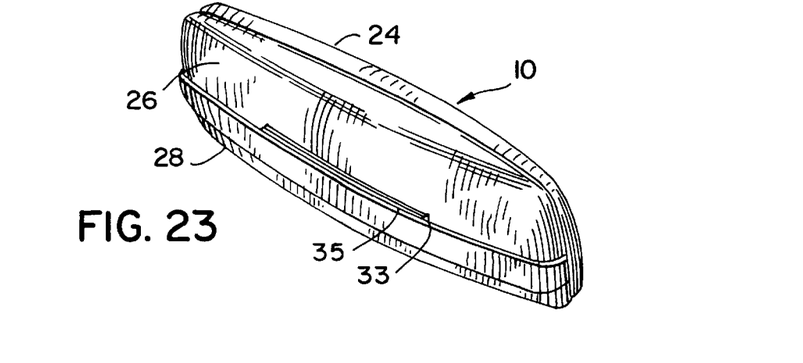
FIG. 23 is a perspective view of the case of FIG. 20 fully closed around the mask.

A variant to the latter embodiment is illustrated in FIGS. 20 through 23, wherein gusset elements are eliminated to reduce the overall thickness of case 10. Thus, as shown in FIGS. 20 and 21, case 10 may be formed of a front panel 24 and upper and lower rear panels 26 and 28 bounded by a single border 29. Closure elements 33 and 35 are provided along lower and upper edges 34 and 36 of panels 24 and 26, respectively, as before. Attachment strips 52 and 54 are secured to attachment regions 56 on either side of case 10 and are configured as described above, including hook regions 58 and loop regions 60 disposed so as to lie in mutually facing relation when attached to attachment assemblies 20 on either side of mask 11. FIGS. 22 and 23 illustrate stages of insertion of mask 11 into case 10 in accordance with this embodiment. As before, insertion of the mask into case 10 begins with separation of closure elements 33 and 35 and inversion of case 10 as shown in FIG. 22. Mask 11 may then be pressed into inverted case 10 and closure elements 33 and 35, once again in mutually facing relation, may be closed over mask 11 to fully envelop the mask and close the case as shown in FIG. 23.

Figure 24:
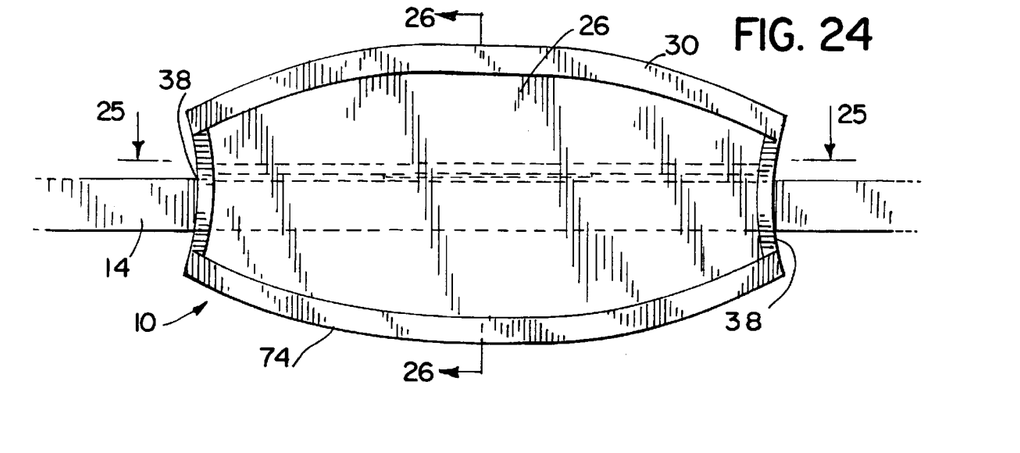
FIG. 24 is a back elevation view of a third preferred embodiment of the inventive case wherein the opening is defined along one edge of the pouch.
Figure 25:
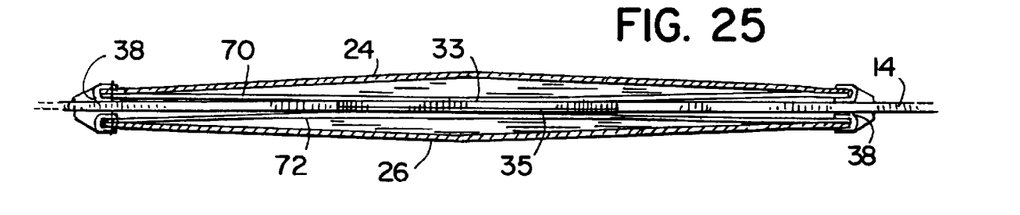
FIG. 25 is a sectional view of the case of FIG. 24 along line 25—25 of FIG. 24, illustrating the construction of the case.
Figure 26:
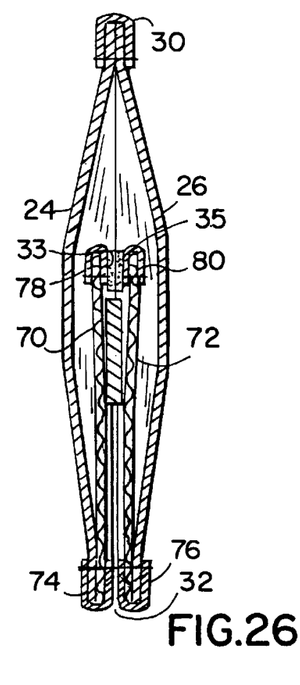
FIG. 26 is a sectional view of the case of FIG. 24 along line 26—26, illustrating the internal components of the case when in their folded position.

FIGS. 24 through 29 represent another preferred embodiment of the inventive case wherein an opening for insertion and removal of the mask is provided along an edge of the pouch. Thus, as best shown in FIGS. 24, 25 and 26, case 10 includes a front panel 24 secured along an upper edge to a rear panel 26. In this embodiment, an integral gusset structure is defined by inner panels 70 and 72 which are interposed between front and rear panels 24 and 26. Inner panels 70 and 72 are preferably a loose net material or a lightweight fabric which promotes drying of mask 11 when placed within case 10 as described below. Front panel 24 and rear panel 26 are joined along their upper edges and preferably surrounded by a border 30 in the manner described above with reference to the previous embodiments. Along its lower edge, front panel 24 is joined to inner panel 70, while rear panel 26 is joined to inner panel 72. Borders 74 and 76 preferably enclose the edges of panels 24 and 70, and 26 and 72, respectively. Side apertures 38 are formed between panels 24, 70 and 26, 72, as best illustrated in FIG. 25. Apertures 38 permit passage of a strap 14 through case 10 as described above. Moreover, edge borders 78 and 80 are preferably sewn along loose edges of inner panels 70 and 72. Hook and loop closure panels 33 and 35 are secured along these edges for maintaining inner panels joined with in the folded position illustrated in FIGS. 24–25 as well as in the protective position shown in FIGS. 28 and 29. In this embodiment, opening 32 is defined between front and rear panels 24 and 26.

Figure 27:
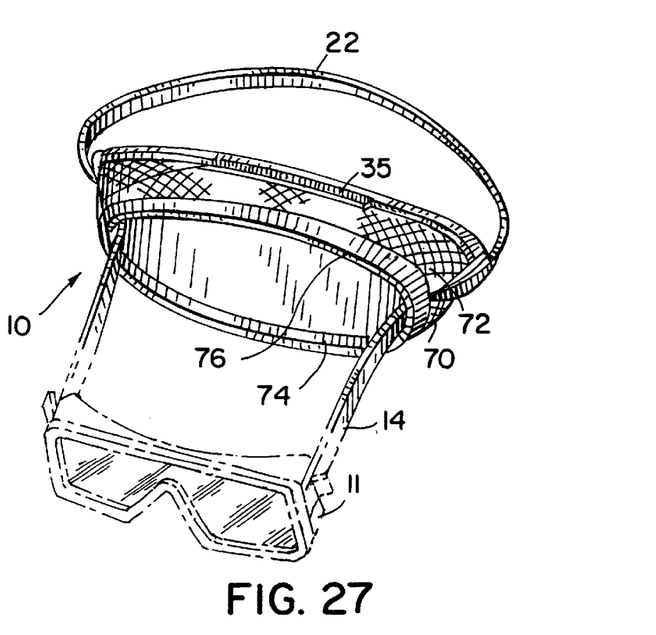
FIG. 27 is a perspective view of the case of FIG. 24 during a first phase of insertion of a mask therein.
Figures 28, 29:
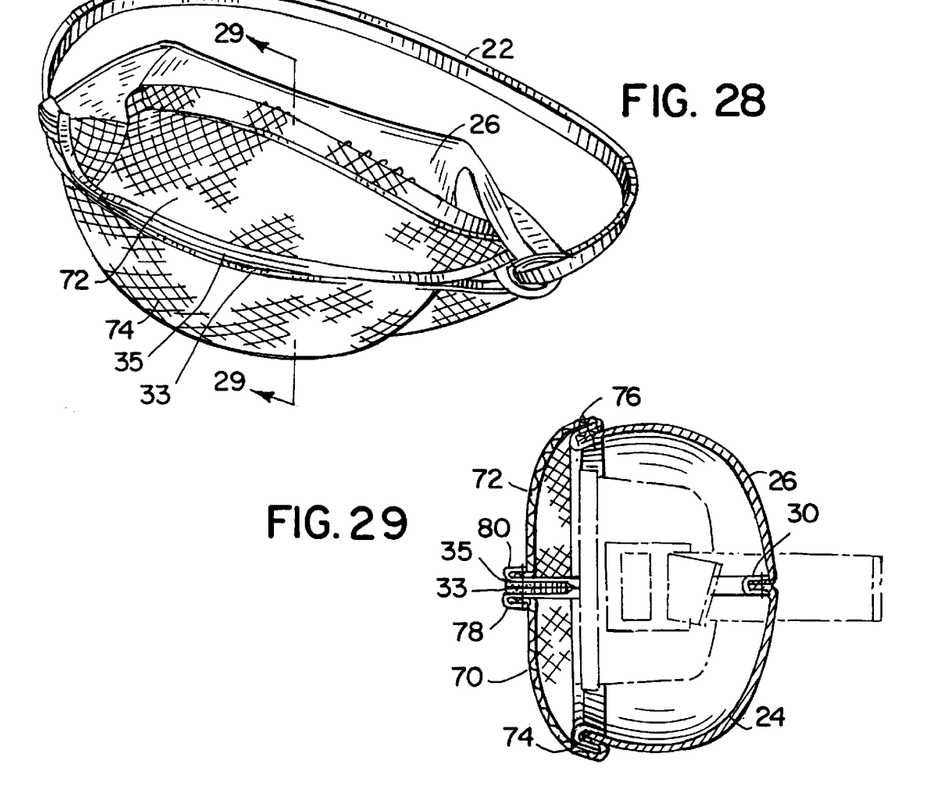
FIG. 28 is a perspective view of the case of FIG. 24 with the mask fully inserted therein.
FIG. 29 is a sectional view of the case of FIG. 28 along line 29—29 showing the orientation of the mask within the closed case.
Figure 30:
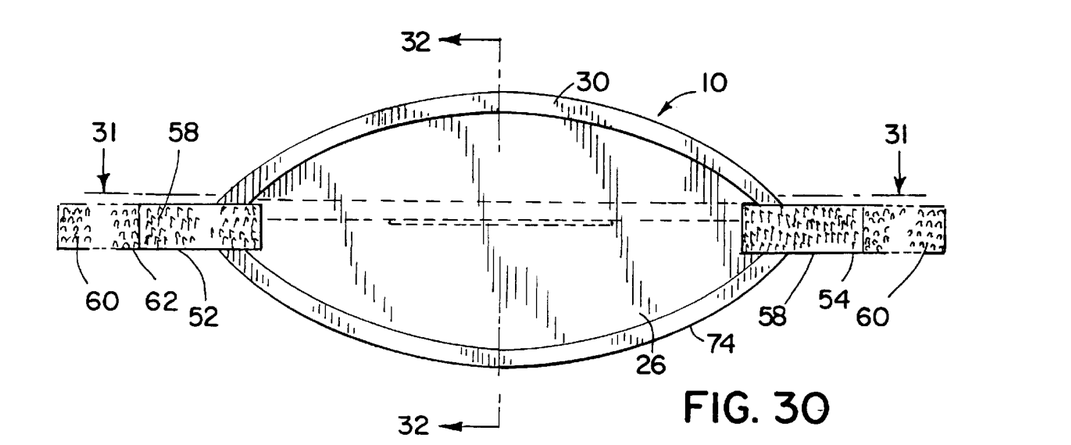
FIG. 30 is a back elevation of a variant of the third embodiment wherein straps are secured to the pouch for subsequent attachment to a mask.
Figure 31:
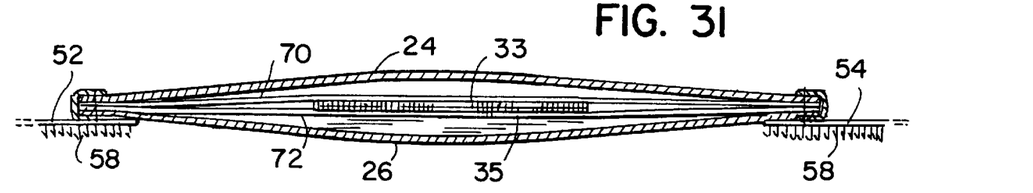
FIG. 31 is a sectional view of the case of FIG. 30 along line 31—31.

Stages of insertion of mask 11 into case 10 are illustrated in FIGS. 27 and 28. As shown in FIG. 27, case 10 is first opened by drawing inner panels 70 and 72 out of the pouch formed by front and rear panels 24 and 26. Closure panels 33 and 35 are detached from one another and the case is inverted and drawn along strap 14 toward mask 11. Mask 11 is then inserted into case 10 and closure panels 33 and 35 may be rejoined, completely enclosing mask 11 within case 10 as best shown in FIG. 29.

FIGS. 30 through 34 represent a variant of the embodiment just described. In this embodiment, rather than apertures 38 for a separable strap 14, first and second attachment straps 52 and 54 are provided, similar to the arrangement described above with reference to FIGS. 13 through 23. In this embodiment, the components of case 10 in this embodiment are essentially identical to those described above with reference to FIGS. 24–29, including front and rear panels 24 and 26, and inner panels 70 and 72 (see FIGS. 30–32).

However, attachment straps 52 and 54 are secured to rear panel 26, such as by stitching in attachment regions 56. Hook and loop attachment regions 58 and 60 are provided along an outer side of straps 52 and 54 in locations allowing these regions to lie in mutually facing relation to one another when straps 52 and 54 are attached to a mask 11 as shown in FIG. 33.

Figures 32, 33:
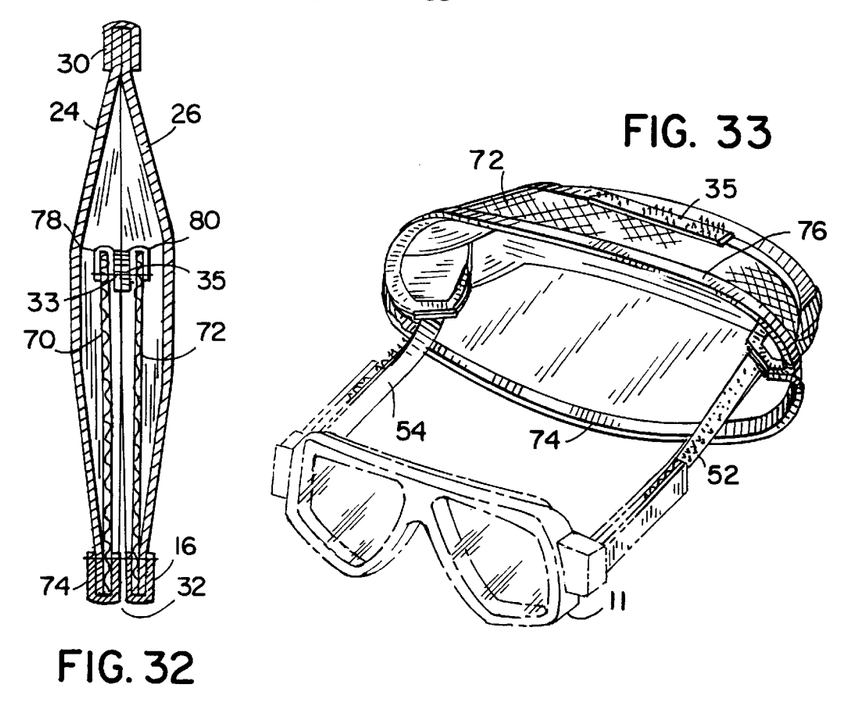
FIG. 32 is a sectional view of the case of FIG. 30 along line 32—32.
FIG. 33 is a perspective view of the case of FIG. 30 during a first phase of insertion of a mask therein.
Figure 34:
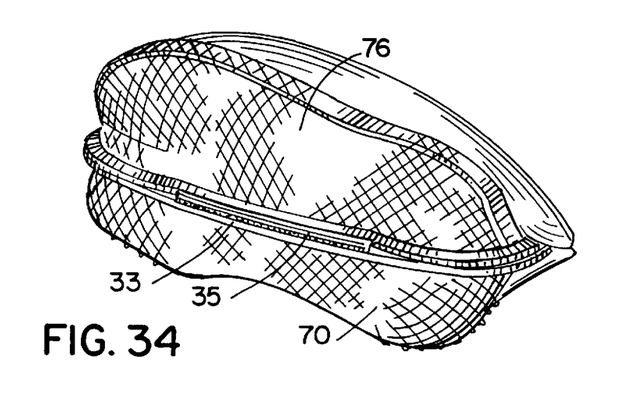
FIG. 34 is a perspective view of the case of FIG. 33 with the mask fully enveloped by the case.

Mask 11 is inserted into case 10 in this embodiment as shown in FIGS. 33 and 34. First, case 10 is inverted by drawing inner panels 70 and 72 out of the pouch formed by front and rear panels 24 and 26, detaching closure panels 33 and 35 from one another. Mask 11 is then pressed into the open case and closure panels 33 and 35 are rejoined to close case 10 around the mask.

Hook portion of the strap at least partially around the back of rear panel 26.

While the foregoing embodiments have been described by way of example, it should be noted that additional modifications may be envisioned by those skilled in the art without departing from the spirit and scope of the appended claims. For example, various closure means may be provided for joining upper and lower rear panels 26 and 28, including devices such as snaps, zippers, buttons, and the like. In addition, while gusset members 42 and 44 have been described as being preferably lighter-weight synthetic fabrics or netting, other elements of case 10 may comprise such materials. Similarly, multi-layered materials may be used for some or all of the panels comprising case 10 where desired. This is particularly true where some or all of the panels of case 10 are used to support advertising indicia or logos (not shown in the Figures.). It is particularly anticipated that certain surfaces of case 10 may provide an excellent platform for such advertising indicia, such as rear panels 26 and 28 or front panel 24. It should also be noted that such indicia may be provided on either inner surfaces of these panels or outer surfaces, or both due to the fact that both inside and outside surfaces of these panels are visible in case 10 due to its inversion as it is converted between its folded, in-use configuration and its storage configuration. Moreover, in the embodiments described above having hook and loop fastening means on straps secured to the pouch, a portion of the hook material may be secured to part or all of rear panel 26, providing enhanced adjustability of the straps, particularly for small users. Finally, it should be noted that the opening (and closure means) of case 10 may be provided in various positions in addition to those described above. For example, a slot-type opening may be formed and disposed to fit against the user's head when in the worn position. Similarly, the opening described above along the lower edge of the case may be configured along an upper edge of the case.

What is claimed is:

1. A case and mask combination, the combination comprising:
   a mask including a frame, a lens supported in the frame, and a strap attached to the frame and configured to partially encircle the head of a user to hold the frame against the user's face, and
   a case including a flexible front panel configured to bear against the user's head when worn;
   a flexible rear panel secured to the front panel along a border region to define a pouch, the pouch having a central opening through which the mask may be inserted into and removed from the pouch; and
   a pair of side apertures being defined on either side of the central opening, the side apertures receiving the strap for holding the case on a central region of the strap, the case being attachable to the strap and positionable in a first, in-use configuration wherein the case is substantially flattened for wearing behind the user's head and in a second, storage configuration wherein the case envelops at least the mask lens.

2. The case of claim 1, wherein at least the front panel is made of a synthetic padding material, whereby the front panel forms a pad interposed between the strap and the user's head when the case is worn behind the user's head in the first configuration.

3. The case of claim 1, wherein the rear panel includes an upper rear panel section and a lower rear panel section, and wherein the central opening is defined between the upper and lower rear panel sections.

4. The case of claim 3, wherein at least a portion of the upper rear panel section overlaps at least a portion of the lower rear panel section.

5. The case of claim 3, further comprising a first closure element secured adjacent to a lower edge of the upper rear panel section and second closure element secured adjacent to an upper edge of the lower rear panel section, the first and second closure elements mutually cooperating to maintain the central opening closed.

6. The case of claim 5, wherein the first and second closure elements comprise a hook and loop fastening system.

7. The case of claim 5, wherein the first and second closure elements are positioned in mutually facing relation in both the first and second configurations of the case.

8. The case of claim 1, wherein the front and rear panels are invertible whereby the case is convertible from the first configuration to the second configuration by inverting the front and rear panels over the mask.

9. The case of claim 1, further comprising a central gusset, the gusset being attached to the front panel and to the rear panel, the gusset being foldable into a collapsed position between the front and rear panels.

10. A convertible case and a mask combination, the case and mask combination comprising:
    a mask including a frame configured to fit securely around a portion of a user's face, at least one lens supported in the frame, the frame having a right side and a left side, the mask including a right and a left strap attachment structure being disposed on the right and left sides of the frame respectively; and
    a case including:
       a flexible first panel;
       a flexible second panel secured to the first panel, the second panel defining with the first panel a convertible pouch, the pouch having an opening through which the mask may be inserted into and removed from the pouch, the pouch having a right and left side; and
       a strap system, the strap system including right and left strap portions configured for attachment to the right and left side of the pouch and to the right and left strap attachment structures respectively, the right and left strap portions extending between the pouch and the right and left attachment structures when the mask and vouch are worn around the user's head; and
    wherein the pouch is collapsible into a first, worn configuration wherein the pouch fits securely against the user's head, the left and right sides of the frame, and the left and right sides of the pouch being proximate the left and right sides of the user respectively, in the first worn configuration, and a second, storage configuration wherein, the left and right portion of the mask fit within the left and right sides of the pouch respectively, when the mask is in the storage configuration, wherein the case includes first and second side apertures defined between the first and second panels, and wherein the strap system includes a unitary strap extending through the first and second apertures.

11. A convertible case and a mask combination, the case and mask combination comprising:

a mask including a frame configured to fit securely around a portion of a user's face, at least one lens supported in the frame, the frame having a right side and a left side, the mask including a right and a left strap attachment structure being disposed on the right and left sides of the frame respectively; and a case including:

a flexible first panel;

a flexible second panel secured to the first panel, the second panel defining with the first panel a convertible pouch, the pouch having an opening through which the mask may be inserted into and removed from the pouch; and strap system, the strap system including first and second strap portions configured for attachment to the pouch and to the first and second strap attachment structures respectively, the first and second strap portions extending between the pouch and the first and second attachment structures when the mask and pouch are worn around the user's head;

wherein the pouch is collapsible into a first, worn configuration wherein the pouch fits securely against the user's head and a second, storage configuration wherein the pouch fits over the mask to cover at least the lens, wherein the opening in the pouch is defined by an edge of the first panel and an edge of the second panel.

* * * * *